United States Patent [19]

Morganson et al.

[11] 4,365,105
[45] Dec. 21, 1982

[54] OLIGOMERIZING 1-OLEFINS WITH A HETEROGENEOUS CATALYST

[75] Inventors: Neal E. Morganson, McCandless Township, Allegheny County; Paul G. Bercik, Penn Township, Westmoreland County, both of Pa.

[73] Assignee: Gulf Research & Development Company, Pittsburgh, Pa.

[21] Appl. No.: 333,305

[22] Filed: Dec. 22, 1981

[51] Int. Cl.$^3$ ................................................. C07C 2/02
[52] U.S. Cl. .................................... 585/525; 585/510
[58] Field of Search .............. 585/512, 513, 521, 523, 585/525, 527

[56] References Cited

U.S. PATENT DOCUMENTS 2,568,209  9/1951  Wackher et al. ............... 585/525 X
4,213,001  7/1980  Madgaukar et al. ........... 585/525 X Primary Examiner—Delbert E. Gantz
Assistant Examiner—Asokkumar Pal
Attorney, Agent, or Firm—Deane E. Keith; Forrest D. Stine; Donald L. Rose

[57] ABSTRACT

An alpha-olefin is oligomerized in the presence of a three-component catalyst comprising a particulate solid adsorbent, boron trifluoride and elemental oxygen. For example, 1-decene is oligomerized to a product predominating in the trimer and tetramer using boron trifluoride, elemental oxygen and silica as the solid adsorbent.

13 Claims, No Drawings

OLIGOMERIZING 1-OLEFINS WITH A HETEROGENEOUS CATALYST

SUMMARY OF THE INVENTION

An alpha-olefin is oligomerized in the presence of a catalyst comprising boron trifluoride, a minute amount of elemental oxygen and a particulate adsorbent material such as silica to a product predominating in those oligomer fractions having viscosities within the lubricating oil range such as the trimer and tetramer of 1-decene.

DESCRIPTION OF THE INVENTION

The oligomer mixtures produced from certain 1-olefins that have been polymerized using boron trifluoride as the catalyst, have been useful as base fluids for preparing lubricants, hydraulic fluids, transmission fluids, transformer fluids and the like, generically designated by the term "functional fluids." The oligomer product of 1-olefins having from four to 12 carbon atoms or mixtures of these have been described as useful for preparing these functional fluids, with the oligomer product of 1-decene being particularly preferred in current usage. The functional fluids that have been prepared from 1-decene for use in motor oils contain various proportions of the trimer, tetramer and pentamer fractions, the dimer having been removed because it possesses significant volatility and low viscosity. However, even this 20 carbon oligomer can be useful as a functional fluid in specific applications.

In the oligomerization reaction, the use of a promoter or co-catalyst with the boron trifluoride has been conventional in order to obtain useful catalytic activity for the boron trifluoride. The co-catalyst complexes with the boron trifluoride to form a coordination compound which is catalytically active for the oligomerization reaction. Included in the list of substances which have been recommended as co-catalysts are various polar compounds including: aliphatic ethers, such as dimethyl ether and diethyl ether; aliphatic alcohols, such as methanol, ethanol, n-butanol and decanol; polyols, such as ethylene glycol and glycerol; water; aliphatic carboxylic acids, such as acetic acid, propanoic acid and butyric acid; esters, such as ethyl acetate and methyl propionate; ketones, such as acetone; aldehydes, such as acetaldehyde and benzaldehyde; and acid anhydrides, such as acetic acid anhydride and succinic anhydride. The use of these boron trifluoride coordination compounds is described in U.S. Pat. Nos. 3,149,178; 3,382,291; 3,742,082, 3,763,244; 3,769,363; 3,780,128; 3,997,621; 4,045,507 and others.

Although these coordination compounds of boron trifluoride are very effective oligomerization catalysts for the higher alpha-olefins, experiments have demonstrated that they possess a significantly reduced activity when they are reused in the oligomerization reactor after recovery from the product stream. Therefore, this inability to reuse the catalyst requires the substantial continuing expense of fresh catalyst and co-catalyst. There are also presented the additional problems not only of a substantial cost of waste treatment and disposal procedures for the spent catalyst but also the possibility of environmental contamination, all of which can make the process prohibitive.

We have discovered a process for the oligomerization of 1-olefins which utilizes a three-component catalyst system comprising a particulate solid adsorbent, elemental oxygen and boron trifluoride. In our process the boron trifluoride can be readily recovered from the oligomer product for reuse in the oligomerization reactor at its original activity without the significant loss in activity as is experienced with the polar compound complexes of boron trifluoride. As a result, catalyst and waste treatment costs are minimized and disposal and environmental problems are substantially avoided. Furthermore, the use of our catalyst system under appropriate reaction conditions results in a high conversion of the 1-olefin to the desired oligomer fractions.

A particulate solid adsorbent is utilized in the oligomerization reactor as one of the components comprising our three-component catalyst system. This solid adsorbent can be positioned in the reactor as a bed for flow-through contact with the reaction liquid or it can be maintained as a slurry in the reaction liquid by suitable agitation in a batch or continuous reaction. When the reaction vessel is pressured with boron trifluoride, a substantial quantity of the boron trifluoride is adsorbed by the solid adsorbent to form an active oligomerization catalyst, as described in U.S. Pat. No. 4,213,001. Since boron trifluoride readily desorbs from the solid adsorbent, a suitable boron trifluoride pressure and a suitable concentration of boron trifluoride in the reaction liquid is maintained during the oligomerization reaction to ensure that the catalytically active solid adsorbent-boron trifluoride combination is maintained throughout the course of the oligomerization reaction.

However, it has been observed that this two-component catalyst comprising the solid adsorbent and the boron trifluoride gradually loses activity after a period of continued use, which aging cannot be conveniently corrected by increasing the boron trifluoride pressure. It is believed that this catalyst aging is the result of gradual physical and chemical changes in the solid adsorbent-boron trifluoride catalyst as it is being used. Unexpectedly, we have discovered that this aging can essentially be prevented if a minute amount of elemental oxygen is fed to the reactor. The silica, boron trifluoride and added elemental oxygen form the three-component catalyst system of our process. Not only does this three-component catalyst system prevent aging of the catalyst, but surprisingly, we have further discovered that a solid adsorbent-boron trifluoride catalyst which has aged in an absence of added elemental oxygen can be regenerated to substantially its original activity merely by introducing the requisite amount of elemental oxygen to the reactor and continuing the reaction.

We have further discovered that the overall conversion of the 1-olefin is significantly improved without substantial change in the selectivity to the various oligomer fractions by the presence of our three-component catalyst system in comparison with the oxygen-free reaction system. As a result of this greater catalyst activity resulting from the use of elemental oxygen, the process can be operated at a greater throughput of the 1-olefin feed as determined by the liquid hourly space velocity. Another benefit in this greater catalyst activity is that the process can be operated with less boron trifluoride in the catalyst and therefore less boron trifluoride fed to the reactor. Moreover, the use of oxygen instead of water, which reacts with the boron trifluoride, as the third component for maintaining catalyst activity, avoids the corrosion-causing hydrogen fluoride and system-plugging borate by-products that result when water is present. Additionally, elemental oxygen is much easier to meter into the system than water.

The elemental oxygen, also commonly called molecular oxygen, or free or uncombined oxygen, which is used in our process can be used in a substantially pure form or it can be mixed with an inert gas such as with nitrogen as in air. The gaseous oxygen is conveniently added to the boron trifluoride feed stream for introduction into the reactor. However, it can also be added as a separate stream to the reactor, or it can be dissolved in the olefin feed stream. Desirably, sufficient oxygen is added to prevent the significant aging of the catalyst which would occur with the two-component catalyst comprising a solid adsorbent and boron trifluoride. Thus, the amount of elemental oxygen added to the reactor suitably can be at least about 25 ppm (parts per million) based on the olefin feed to the reactor, with at least about 50 ppm oxygen based on the olefin feed being preferred as the minimum amount of elemental oxygen that is fed to the reactor. A substantial excess of added elemental oxygen does not appear to provide a benefit to the process. Therefore, for convenient operation, it is preferred that the maximum oxygen addition be about one weight percent based on the olefin feed, and most preferably a maximum amount of about 0.25 weight percent oxygen based on the olefin feed.

As is the case with the prior art oligomerizations, 1-decene is the most preferred alpha-olefin for preparing synthetic lubricants and related functional fluids by our novel process. However, 1-olefins having from three to about 18 carbon atoms and preferably about eight to about 12 carbon atoms or various combinations of these alpha-olefins can also be used. The straight-chain olefins, generally referred to as the normal 1-olefins, are preferred; however, branched-chain 1-olefins can comprise a portion or all of the 1-olefin feed. A potentially significant result in varying the molecular structure of the 1-olefin is an effect on the properties of the resulting oligomer, including the viscosity, pour point and volatility, and it is for this reason that the straight-chain 1-olefins are preferred. When a 3- or 4-carbon olefin is used, it is generally preferred that this lower olefin be co-oligomerized with at least about 20 mol percent of one or more of the higher olefins in order to obtain the desired oligomer mixture.

In its broadest aspect, the lubricating oil range to which our process is directed varies between about 20 and about 50 carbon atoms, and more particularly between about 24 and 42 carbon atoms, and most preferably about 30 to about 40 carbon atoms. Our process is therefore preferably carried out under appropriate conditions to obtain the maximum oligomer selectivity within the desired range of carbon numbers. One of the particular benefits of our three-component catalyst system is that high product selectivity within the lubricating oil range is readily obtained, and under appropriate conditions the selectivity is even enhanced. Since it is difficult to separate or even determine by analysis the different oligomer fractions having about 50 carbon atoms and higher, reference herein to an oligomer fraction having about 50 carbon atoms is intended to include the possible presence of minor amounts of one or more oligomer fractions having a higher number of carbon atoms.

Any solid adsorbent material, inorganic or organic which has a surface area of at least about 0.1 $m^2/g$ and which is insoluble in the reaction liquid can be used as the solid adsorbent in our process. The class of inorganic adsorbents include silica, the silica-aluminas, silica-zirconia, silica-magnesia, silica-thoria, alumina, magnesia, zirconia, activated carbon, the zeolites, silicon carbide, silicon nitride, titania, aluminum-aluminum phosphate, zirconium phosphate, thoria, the magnesia-aluminas such as magnesium aluminate, zinc aluminate, pumice, naturally occurring clays, such as diatomaceous earth, and the like. The class of organic adsorbents includes porous polyvinyl alcohol beads, porous polyethylene glycol beads, the macroreticular acid cation exchange resins, such as the sulfonated styrene-divinylbenzene copolymer exchange resins (for example, Amberlyst-15 and Amberlite-XN1040 supplied to Rohm and Haas Company, Philadelphia, Pa.), and the like. We prefer silica itself or a composition comprising at least about 50 percent silica as the solid absorbent.

The solid adsorbent portion of the three-component catalyst is preferably used as a fixed bed of relatively uniformly sized particles in a flow-through reactor. The external surface area of the solid adsorbent is a more significant factor with regard to catalyst activity than its pore volume. As a result, the particle size can be of particular significance. In general, the smaller the particle size the greater the activity at constant catalyst volume; however, a catalyst bed formed from too finely sized particles tends to restrict the flow of the reaction stream, as indicated by a significant pressure drop across the catalyst bed. For these rasons the particle size of the solid adsorbent is preferably at least about 100 mesh (0.15 mm) and most preferably at least about 50 mesh (0.3 mm). The maximum particle size is preferably about 3 mesh (6.7 mm) and most preferably about 10 mesh (20 mm). However, useful oligomer products can be prepared with solid adsorbent outside these limits of particle size. We have found 15/25 mesh (0.7-1.3 mm) silica to be particularly suitable when reactivity, pressure drop, and heat transfer considerations are taken into account. When a slurry of the catalyst is used in a reactor, not only the particle size but also the amount of the catalyst exerts a significant effect on the rate of reaction.

The reaction temperature also exerts a significant effect on the reaction. As the temperature increases at constant contact time, both the conversion and the selectivity to oligomers higher than the dimer decreases while the amount of the dimer increases. For this reason it is desirable that the maximum reaction temperature be about 150° C., preferably no higher than about 100° C., and most preferably no higher than about 50° C. On the other hand, although the reaction can be carried out at a temperature as low as about $-50°$ C., it is preferred that the minimum operating temperature be at least about $-10°$ C. We believe that the temperature affects the solubility of the oxygen and the boron trifluoride in the reaction liquid and also affects adsorption on the solid adsorbent and that these cumulative effects help to cause the inverse relationship of temperature with conversion. In general, a temperature gradient exists across the catalyst bed during the reaction by as much as 10° C. or more. The term "reaction temperature," therefore, refers to the highest temperature or "hot spot" temperature in the catalyst bed. On the other hand, a uniform temperature will be present in a slurry reactor.

Since boron trifluoride continuously desorbs from the solid adsorbent during the course of the reaction, it is necessary to feed boron trifluoride to the reactor, either directly or with the olefin feed, to ensure that sufficient boron trifluoride is present in the catalyst for the oligomerization reaction. The adsorption and desorption of the boron trifluoride is affected by many operating variables, including temperature, pressure, nature and particle size of the solid adsorbent, the composition of the feed and the reaction mixture, and the like. The minimum feed rate of the boron trifluoride will therefore depend on the particular operating conditions in any specific situation.

Typically, the born trifluoride feed rate is at least equal to its solubility in the reaction liquid at the particular conditions of operation, and preferably is in excess of its solubility in the reaction liquid. The solubility of the boron trifluoride in the reaction liquid is significantly affected by the partial pressure of boron trifluoride in the gas phase. We have also found that the boron trifluoride partial pressure exerts a significant effect on the amount of boron trifluoride adsorbed by the solid adsorbent and on the resulting catalyst activity. As a result, variations in pressure result in significant variations in conversion but with only moderate variations in product selectivity. Pure boron trifluoride gas can be utilized or it can be used in admixture with the elemental oxygen. It can also be mixed with an inert gas such as nitrogen, argon, helium, and the like. When used as a mixture with an inert gas, it is preferred that the boron trifluoride comprise at least about 10 mol percent of the gas mixture.

Because of the many variables involved, as indicated, it is difficult to specify a feed rate for the boron trifluoride for any particular set of operating variables. It is more meaningful to indirectly indicate the amount of boron trifluoride fed to the reactor by specifying the partial pressure of boron trifluoride in the reactor. Even though the oligomerization reaction can be carried out at atmospheric pressure when using pure boron trifluoride, we find it desirable to maintain a partial pressure of boron trifluoride in the reactor of at least about 10 psig (0.17 MPa) for suitable catalyst activity, and preferably at least about 50 psig (0.44 MPa) for superior catalyst activity. Partial pressures of boron trifluoride as high as about 500 psig (3.55 MPa) and higher, such as about 1,000 psig (7.03 MPa), can be utilized. Elevated pressure can result in increased catalyst activity, causing increased structural isomerization of the olefin reactants and products and resulting in higher viscosity fluids.

When the fixed-bed reactor is used, suitable results can be obtained with a relatively high throughput of the liquid reactant olefin. In fact, we find that conversion of the 1-olefin is only moderately decreased as the space velocity of the reactant liquid is increased. In the case of a 1-decene feed, an increase in space velocity results in an increase in the dimer and a corresponding decrease in the higher oligomer fractions. The oligomerization reaction in a fixed bed can conveniently be carried out within the broad range of liquid hourly space velocities, that is, the volume of the liquid feed per volume of catalyst per hour, of between about 0.1 and about 50 hr.$^{-1}$, but preferably the reaction is carried out within the range of about 0.5 and about 10 hr.$^{-1}$, and most preferably about one hr.$^{-1}$. These ranges for space velocity are also applicable with a flow-through slurried catalyst system.

Since the oligomerization reaction involves a series of competing reactions, monomer with monomer, monomer with dimer, dimer with dimer, monomer with trimer, etc., resulting in a series of product oligomer fractions, the particular reaction conditions utilized will depend on the 1-olefin feed that is used and the product oligomer fraction or fractions, that is desired. Although it is preferred that the reaction be carried out at maximum conversion and optimum selectivity to desired products, such may not be possible. However, the overall selectivity may be substantially improved if those oligomer fractions lower than the desired oligomer fractions are recovered from the product stream and recycled to the feed stream for further reaction. Since the oligomer fractions which are heavier, i.e. have a greater molecular weight, than the desired fractions represent a process loss, it may be desirable to operate the oligomerization reaction under conditions which minimize the undesired heavier fractions, even though this may increase the amount of product recycle.

The expression "reaction liquid" as used herein refers to the 1-olefin monomer or mixture of monomers, any inert solvent, if present, and the oligomer products which will be present once reaction has started. It is possible to carry out the reaction in the presence of up to about 80 percent, preferably up to about 60 percent, of a suitable inert solvent. Suitable solvents can be used for temperature control and for product control. Such solvents tend to slow down the various reaction rates and can be utilized in conjunction with the different variables to control the course of the reaction and the nature of the reaction products. Suitable solvents can be selected from aliphatic hydrocarbons such as pentane, hexane, heptane, and the like, and aromatic hydrocarbons, such as benzene, toluene, chlorobenzene, and the like. The solvent, if utilized, should be liquid at reaction conditions and should be substantially lower in boiling point than any other component to simplify separation upon completion of the reaction.

In a slurried catalyst system, the solid adsorbent is maintained as a slurry in the reaction liquid by suitable agitation. In the continuous slurry procedure, a suitable porous plate is positioned between the reaction liquid and the reactor outlet. A continuous stream of reaction product is removed at a rate to provide a predetermined desirable average residence time in the reactor. Since the filter plate prevents the egress of the powdered adsorbent, the product stream is free of solids. As the product is removed, make-up 1-olefin is injected into the reactor inlet to provide a constant liquid volume in the reactor. The particle size of the adsorbent, the openings in the filter plate and the vigor of the agitation are appropriately intercorrelated to ensure that the absorbent particles neither block the filter openings nor cake up on the filter plate. The batch method can be carried out in the same equipment, with the catalyst remaining in the reactor between batches, or if a filter plate is not used, the slurry can be removed from the reactor at the termination of a batch, filtered, and the catalyst returned for the next batch.

The reaction product which is removed from the reactor, whether a solid-bed reactor or a slurried catalyst reactor, contains unreacted feed olefin, the various product oligomer fractions, any impurities which were originally present in the feed olefin, inert solvent when used, dissolved boron trifluoride gas, and a small amount of dissolved oxygen. The amount of boron trifluoride in the product liquid will, in general, fall within the range of between about 0.1 and about 20 weight percent, depending upon the amount of boron trifluoride that is fed to the reactor, and usually in the lower end of this range. This boron trifluoride can be readily separated from the liquid product in nearly quantitative yield by subjecting the product solution to a vacuum and bubbling nitrogen through the liquid at about 100° C., or by any other appropriate procedure. The separated recycled boron trifluoride is reusable in the process without any change in the activity of the catalyst. The elemental oxygen can also be separated from the reaction product together with the boron trifluoride or as a separate stream and recycled, if desired. When the oxygen is recycled, it may be necessary to bleed off a portion to prevent buildup of inert gases, such as nitrogen, in the system. Traces of boron trifluoride remaining in the product after the separation can be removed from the reaction product with a water wash. The liquid reaction product can then be hydrogenated to eliminate double-bond unsaturation either before or after its separation into the desired fractions.

DESCRIPTION OF PREFERRED EMBODIMENTS

The following experiments were carried out in a vertically mounted, stainless steel reactor one inch (2.54 cm) in internal diameter and ten feet (305 cm) in length. The reactor was fitted with eleven evenly spaced thermocouples to monitor the temperature in the reactor bed. The 1-decene reactant was pumped into the bottom of the reactor and a dry boron trifluoride-oxygen mixture was injected into the 1-decene feed line immediately before it entered into the reactor. The product stream was collected in a 500 cc receiver.

The 1-decene, which typically contained about 1.0 to 1.5 percent saturates and other olefins, was dried over molecular sieves. The solid adsorbent was 10–20 mesh Davison Grade 59 silica having a B.E.T. area of about 250 m$^2$/g, which was calcined at 1000° F. (538° C.). The reactor was packed with about 1,475 cc of the silica, and the boron trifluoride/oxygen gas mixture was injected into the 1-decene feed line going to the reactor. The maximum temperature in the catalyst bed varied between 10° and 15° C. except where noted. Product analysis was carried out with a liquid or gas chromatograph as appropriate. The flow rate of the boron trifluoride gas in the following examples has been standardized to one atmosphere pressure and a temperature of 60° F. (15.6° C.).

EXAMPLES 1–5

A series of experiments were carried out to compare the effects of water, nitrogen and oxygen in a boron trifluoride-silica catalyst system. The 1-decene was fed into the bottom of the reactor and the boron trifluoride, and the other components were fed to the reactor with the 1-decene. Product analyses were taken after steady-state conditions were reached. The feed rates, reaction conditions and product analysis are set out in Table I.

TABLE I

| Example | 1 | 2 | 3 | 4 | 5 |
|---|---|---|---|---|---|
| 1-Decene feed, g/hr | 995 | 995 | 997 | 1,004 | 995 |
| Water content, ppm | 50 | 50 | 50 | 50 | — |
| BF$_3$ feed, wt %[a] | 5.1 | 4.2 | 4.2 | 3.9 | 4.1 |
| N$_2$ feed, ppm[a] | — | 4,600 | — | — | — |
| Air feed, ppm[a] | — | — | 4,675 | 4,644 | 3,905 |
| Oxygen feed, ppm[a] | — | — | 982 | 975 | 820 |
| Outlet pressure, psi | 206 | 202 | 203 | 104 | 102 |
| Max. temp., °C. | 24 | 22 | 38 | 28 | 28 |
| Conversion, % | 91.6 | 86.9 | 95.1 | 92.8 | 93.0 |
| Product analysis | | | | | |
| C$_{20}$ | 12.7 | 12.9 | 14.5 | 13.6 | 14.0 |
| C$_{30}$ | 53.1 | 55.0 | 55.5 | 57.3 | 58.9 |
| C$_{40}$ | 17.9 | 14.7 | 18.7 | 17.1 | 16.8 |

TABLE I-continued

| Example | 1 | 2 | 3 | 4 | 5 |
|---|---|---|---|---|---|
| C$_{50}$ | 6.6 | 3.1 | 5.2 | 3.5 | 3.0 |

[a] based on 1-decene feed

In Examples 6–10, boron trifluoride was recovered from the product stream and was recycled and fed to the reactor together with about two to four percent fresh, make-up boron trifluoride.

EXAMPLE 6

This example, which utilized 1-decene and an excess of boron trifluoride with no elemental oxygen in the reactor, demonstrated catalyst aging as evidenced by a substantial reduction in the percent conversion of the 1-decene feed over a relatively short period of time. The 1-decene was fed into the bottom of the reactor at a liquid hourly space velocity of 0.90 per hour. Boron trifluoride was injected into the 1-decene feed line at a rate of 4.6 weight percent boron trifluoride based on the 1-decene. The reactor was operated at an outlet pressure of 212 psig (1.56 MPa). After operating for four hours to ensure stable operation, regular analyses of the reaction products were carried out over a twenty-hour period. During this period the conversion of 1-decene dropped from 96.2 percent to 82.3 percent, due to catalyst aging. The results are set out in Table II.

EXAMPLE 7

The experiment of the preceding example was continued at the same conditions except that the feed of boron trifluoride was increased to 4.9 percent based on the 1-decene, and 248 ppm of elemental oxygen based on the 1-decene feed was added to the boron trifluoride feed stream. After a short time lag, a striking improvement in the conversion resulted. The results are set out in Table II.

TABLE II

| | Example 6 | | Example 7 | |
|---|---|---|---|---|
| Time, Hours | O$_2$, ppm | Conversion, % | O$_2$, ppm | Conversion, % |
| 0 | 0 | 96.2 | 248 | 82.3 |
| 2 | 0 | 95.7 | 248 | 79.1 |
| 4 | 0 | 94.6 | 248 | 85.0 |
| 6 | 0 | 92.4 | 248 | 90.7 |
| 8 | 0 | 91.9 | 248 | 92.4 |
| 12 | 0 | 89.4 | 248 | 93.1 |
| 16 | 0 | 86.4 | 248 | 92.4 |
| 20 | 0 | 82.3 | 248 | 92.4 |
| 26 | — | — | 248 | 93.2 |
| 36 | — | — | 248 | 93.5 |
| 46 | — | — | 248 | 93.3 |

In another experiment similar to Example 6, using different conditions and feed rates with 40/50 mesh silica and 6.15 weight percent boron trifluoride and no oxygen, the conversion of 1-decene decreased from 88.1 percent to 58.1 percent after 54 hours.

EXAMPLE 8

The experiment of Example 7 was continued except that the oxygen feed rate was reduced to 236 ppm based on the 1-decene. After 1.8 days of operation, the conversion had decreased from 93.3 percent to 91.0 percent.

EXAMPLE 9

The experiment using the conditions of Example 8 was continued except that the oxygen feed rate was reduced to 150 ppm based on the 1-decene. After 1.1 days of operation, the conversion decreased from 91.0 percent to 85.3 percent.

EXAMPLE 10

In this example, unreacted 1-decene was recovered from the product stream and recycled to the feed stream and mixed with fresh 1-decene feed. The recycle stream contained 28.3 weight percent 1-decene, 22.5 percent decane, 45.8 percent of a 20 carbon component, and 3.4 percent of a 30-carbon component, the combined 1-decene stream was fed to the reactor at a liquid weight space hourly velocity of 1.9, of which 0.9 was fresh 1-decene and 1.0 was recycle 1-decene. Boron trifluoride was fed at a rate of 3.67 percent based on the 1-decene, and oxygen was fed at a rate of 376 ppm based on the 1-decene. The conversion of the 1-decene was 75.8 percent. The product distribution and the trimer to tetramer ratio is compared with the product distribution from Examples 6–9 in Table III.

TABLE III

| Example | 6 | 7 | 8 | 9 | 10 |
|---|---|---|---|---|---|
| Selectivity, Wt % | | | | | |
| $C_{20}$ | 15.5 | 13.4 | 12.4 | 11.7 | 5.9 |
| $C_{30}$ | 67.2 | 63.3 | 64.4 | 67.2 | 75.4 |
| $C_{40}$ | 14.8 | 19.2 | 19.1 | 17.7 | 16.3 |
| $C_{50}$ | 2.5 | 4.4 | 4.1 | 3.4 | 2.3 |
| $C_{30}/C_{40}$ | 3.9 | 2.7 | 2.8 | 3.2 | 4.2 |

It is noted from Table III that when 1-decene recycle is used, the overall conversion is lowered, but that this occurs with an increase in selectivity to the trimer and an increase in the trimer to tetramer ratio.

It is to be understood that the above disclosure is by way of specific example and that numerous modifications and variations are available to those of ordinary skill in the art without departing from the true spirit and scope of the invention.

We claim:

1. The process for oligomerizing a 1-olefin having from three to about 18 carbon atoms and mixtures thereof which comprises contacting said 1-olefin in a reactor with a catalyst comprising a solid adsorbant in particulate form in the presence of boron trifluoride and between about 25 ppm and about one weight percent elemental oxygen based on the 1-olefin at a temperature between about −50° and about 150° C.

2. The process for oligomerizing a 1-olefin having from three to about 18 carbon atoms and mixtures thereof in accordance with claim 1 in which a stream of the 1-olefin is introduced into the reactor and is contacted with the catalyst, and a product stream is removed from the reactor.

3. The process for oligomerizing a 1-olefin having from three to about 18 carbon atoms and mixtures thereof in accordance with claim 2 in which the solid adsorbent has a particle size between about 3 and about 400 mesh (about 0.075 and about 6.7 mm).

4. The process for oligomerizing a 1-olefin having from three to about 18 carbon atoms and mixtures thereof in accordance with claim 2 in which the solid adsorbent comprises from about 50 to 100 weight percent silica.

5. The process for oligomerizing a 1-olefin having from three to about 18 carbon atoms and mixtures thereof in accordance with claim 2 in which the partial pressure of boron trifluoride in the reactor is between about atmospheric and about 1,000 psig (7.03 MPa).

6. The process for oligomerizing a 1-olefin having from three to about 18 carbon atoms and mixtures thereof in accordance with claim 2 in which the alpha-olefin is 1-decene.

7. The process for oligomerizing a 1-olefin having from three to about 18 carbon atoms and mixtures thereof in accordance with claim 2 in which the temperature is between about −10° and about 50° C.

8. The process for oligomerizing a 1-olefin having from three to about 18 carbon atoms and mixtures thereof in accordance with claim 2 in which the partial pressure of boron trifluoride in the reactor is between about 50 and about 500 psig (about 446 and about 3,540 kPa).

9. The process for oligomerizing a 1-olefin having from three to twelve carbon atoms and mixtures thereof in accordance with claim 2 in which the 1-olefin is flowed through the reactor in contact with a bed of the solid adsorbent at a liquid hourly space velocity between about 0.1 and about 50 hour$^{-1}$.

10. The process for oligomerizing a 1-olefin in accordance with claim 2 in which the solid adsorbent has a particle size between about 10 and about 50 mesh (about 0.3 and about 2.0 mm).

11. The process for oligomerizing a 1-olefin having from three to about 18 carbon atoms and mixtures thereof in accordance with claim 2 in which oxygen is fed to the reactor at the rate of between about 50 ppm and about 0.25 weight percent based on the 1-olefin fed to the reactor.

12. The process for oligomerizing a 1-olefin having from three to about 18 carbon atoms and mixtures thereof in accordance with claim 2 in which boron trifluoride is recovered from the product stream and is recycled to the reactor feed.

13. The process for oligomerizing a 1-olefin having from three to about 18 carbon atoms and mixtures thereof in accordance with claim 2 in which elemental oxygen is recovered from the product stream and is recycled to the reactor feed.

* * * * *